US00PP20180P3

(12) United States Plant Patent
Elst

(10) Patent No.: US PP20,180 P3
(45) Date of Patent: Jul. 14, 2009

(54) *ESCALLONIA* PLANT NAMED 'JAMIE'

(50) Latin Name: ***Escallonia* hybrid**
Varietal Denomination: Jamie

(76) Inventor: Frank Elst, Grote Heistraat 25, 4884 JA Wernhout (NL)

( * ) Notice: Subject to any disclaimer, the term of this patent is extended or adjusted under 35 U.S.C. 154(b) by 0 days.

(21) Appl. No.: 11/982,017

(22) Filed: Nov. 1, 2007

(65) Prior Publication Data

US 2009/0119811 P1 May 7, 2009

(51) Int. Cl.
*A01H 5/00* (2006.01)

(52) U.S. Cl. ..... Plt./226
(58) Field of Classification Search ..... Plt./226
See application file for complete search history.

(56) References Cited

U.S. PATENT DOCUMENTS

PP4,142 P * 11/1977 Gavello ..... Plt./226
PP4,918 P * 11/1982 Gavello ..... Plt./226

OTHER PUBLICATIONS

UPOV ROM GTITM Computer Database, GTI Jouve Retrieval Software Feb. 2008 Citation(s) for 'Jamie'.*

* cited by examiner

*Primary Examiner*—Susan B McCormick Ewoldt
(74) *Attorney, Agent, or Firm*—Penny J. Aguirre

(57) ABSTRACT

A new cultivar of *Escallonia,* a branch mutation of 'Red Dream', characterized by its compact, prostrate, spreading growth habit combined with its grayed orange stems, its rose pink flowers in mid summer, its tolerance to wind, rain, and drought, and its ease of propagation by softwood cuttings.

2 Drawing Sheets

Botanical classification: *Escallonia* hybrid.
Variety denomination: 'Jamie'.

BACKGROUND OF THE INVENTION

The present invention relates to a new and distinct cultivar of hybrid *Escallonia* and will be referred to hereafter by its cultivar name, 'Jamie'. 'Jamie' is a new cultivar of *Escallonia* shrub grown for use as a landscape plant.

The inventor discovered 'Jamie' in a container in a nursery Zundert, The Netherlands in summer of 2004. The new cultivar arose as a naturally occurring branch mutation of *Escallonia,* 'Red Dream' (not patented).

Asexual reproduction of the new cultivar was first accomplished by the inventor using softwood stem cuttings in August of 2004 in Wernhout, The Netherlands. The characteristics of 'Jamie' have been determined to be stable and are reproduced true to type in successive generations.

SUMMARY OF THE INVENTION

The following traits have been repeatedly observed and represent the characteristics of the new cultivar as grown outdoors in trial beds and in containers in Wernhout, The Netherlands. These attributes in combination distinguish 'Jamie' as a unique cultivar of *Escallonia.*

1. 'Jamie' exhibits a compact, prostrate, spreading habit.
2. 'Jamie' exhibits dark green, glossy foliage.
3. 'Jamie' exhibits stems and petioles that are grayed-orange in color.
4. 'Jamie' is tolerant to rain, wind and drought.
5. 'Jamie' is readily propagated by softwood cuttings.
6. 'Jamie' blooms in mid summer with panicles of rose pink tubular flowers.

'Jamie' is primarily unique in comparison to other cultivars of *Escallonia* for its prostrate, spreading growth habit. The parent plant of 'Jamie', 'Red Dream', has similar flowers and bloom habit, however 'Red Dream' has an upright growth habit and leaves that are not as glossy. 'Jamie' can also be compared to the cultivar 'C. F. Ball' (not patented). In comparison to 'Jamie', 'C. F. Ball' has flowers that are more red in color, an upright growth habit, and small leaves that are lighter green in color.

BRIEF DESCRIPTION OF THE DRAWING

The accompanying colored photographs illustrate the overall appearance and distinct characteristics of the new *Escallonia* as grown outdoors in 2-liter containers in Wernhout, The Netherlands.

Figure 1:
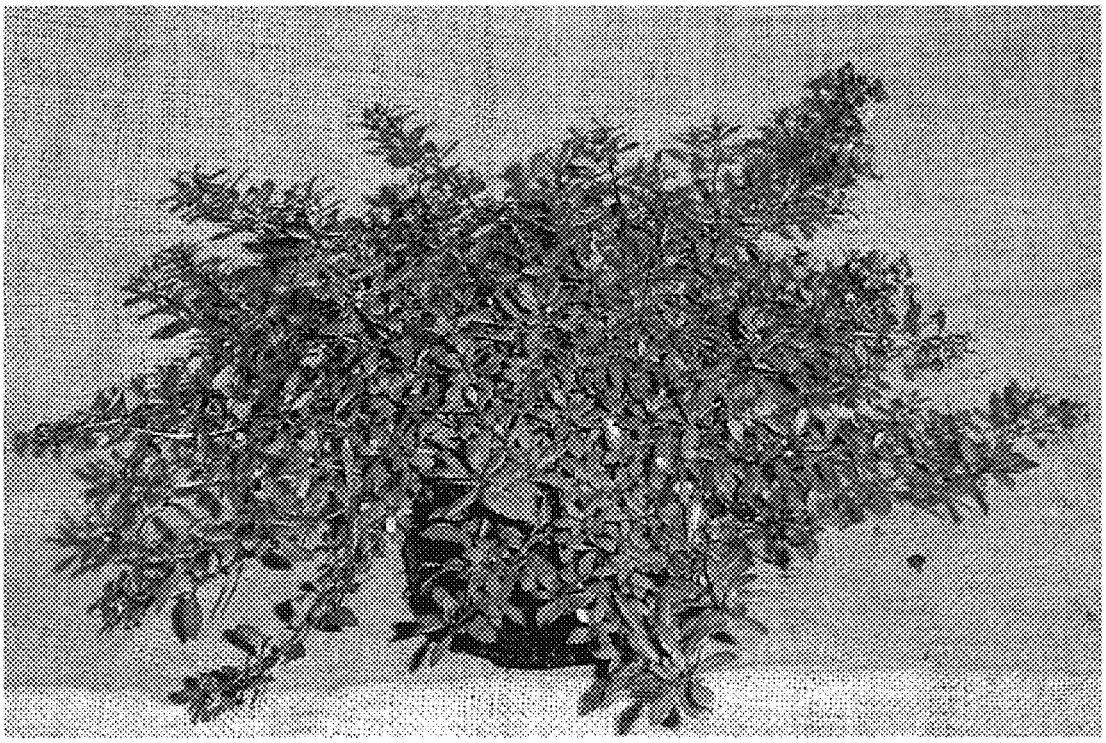
FIG. 1 and FIG. 3 were taken of a plant about 13 months in age and FIG. 2 was taken of a plant about 11 months in age.

The photograph in FIG. 1 illustrates the overall appearance of 'Jamie' in bloom.

Figure 2:
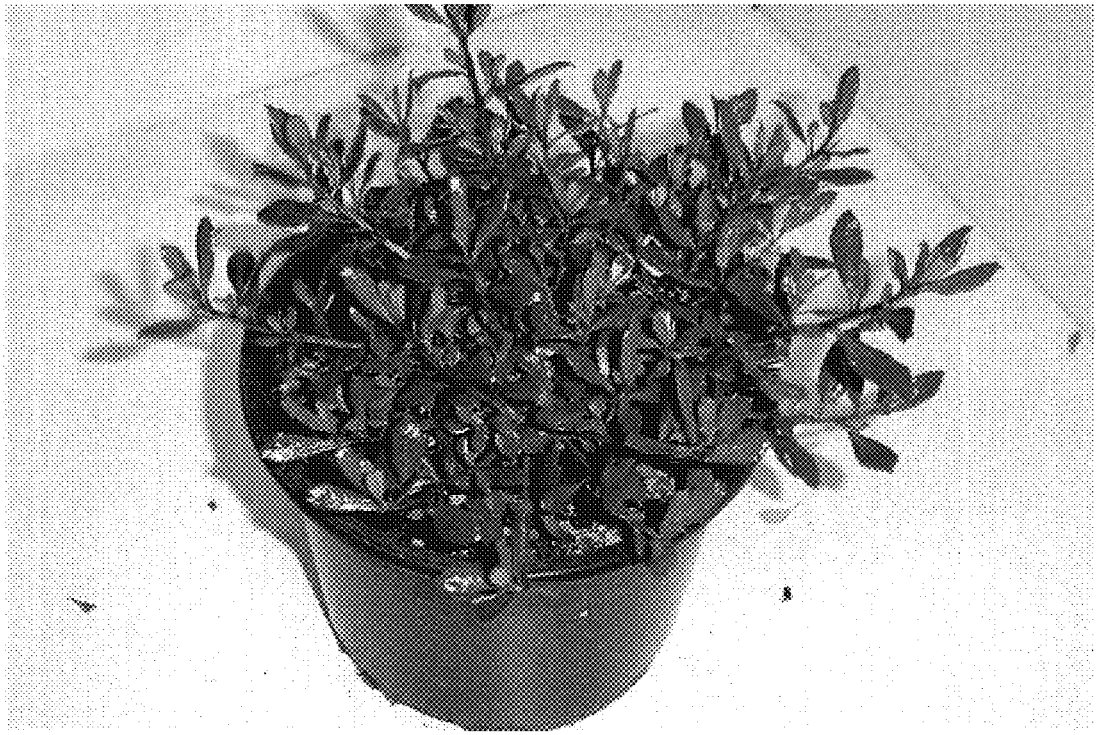

The photograph in FIG. 2 provides a close-up view of the foliage and plant habit of 'Jamie'.

Figure 3:
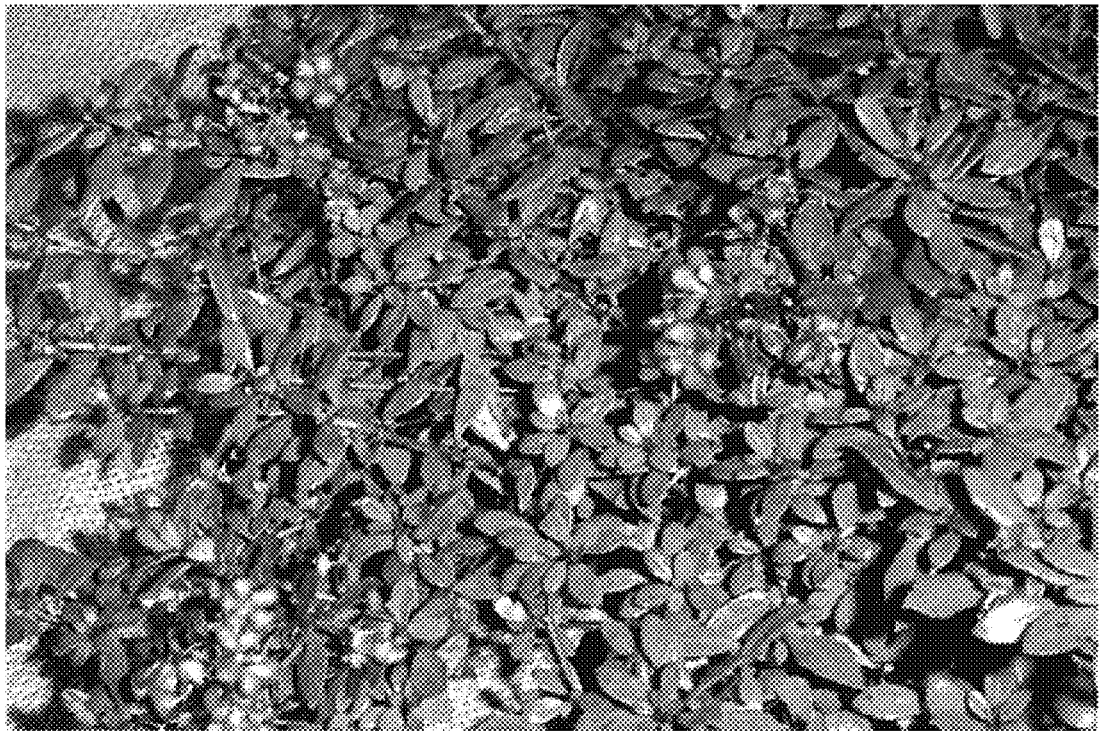

The photograph in FIG. 3 provides a close-up view of the flowers of 'Jamie'.

The colors in the photographs are as close as possible with the digital photography techniques utilized and the color values cited in the detailed botanical description accurately describe the colors of the new *Escallonia.*

DETAILED BOTANICAL DESCRIPTION

The following is a detailed description of 2 year-old plants of the new cultivar as grown outdoors in 2 liter containers in Wernhout, The Netherlands. The plants were grown with an average day temperature of 12° to 25° C. and an average night temperature of 2° to 15° C. under ambient light. The phenotype of the new cultivar may vary with variations in environmental, climatic, and cultural conditions, as it has not been tested under all possible environmental conditions. The color determination is in accordance with the 2001 R.H.S. Colour Chart of The Royal Horticultural Society, London, England, except where general color terms of ordinary dictionary significance are used.

General Description:

*Blooming period.*—Blooms in July and August in Wernhout, The Netherlands.

*Plant habit.*—Compact, evergreen shrub with a prostrate, spreading growth habit.

*Culture.*—Grows well in rich, well-drained soils in full sun to partial shade and is tolerant to drought, rain, wind and salt.

*Height and spread.*—Reaches about 40 cm in height and 60 cm width.

*Hardiness.*—Cold hardy to U.S.D.A. Zone 7, withstands temperatures of at least 35° C.

*Diseases resistance.*—No particular resistance or susceptibility has been observed.

*Loot description.*—Fibrous.

Growth and Propagation:

*Propagation.*—Softwood stem cuttings.

*Root initiation.*—Roots develop in 14 to 21 days in summer under greenhouse conditions on a mist bench without supplemental lighting.

*Root development.*—A blooming, well developed plant is produced in a 2 liter container in about 13 months.

*Growth rate.*—Moderate.

Stem Description:

*Stem shape.*—Round.

*Stem strength.*—Strong.

*Stem color.*—166B to 166C.

*Stem size.*—Lateral branches average about 12.5 cm in length and 2 mm in width.

*Stem surface.*—Smooth, slightly glossy.

*Stem aspect.*—Initially upright, becoming horizontal.

*Internode length.*—Average of 8 mm.

*Branching.*—Average of 38 lateral branches as grown in a 2 liter container, no pinching is required.

Foliage Description:

*Leaf shape.*—Obovate.

*Leaf division.*—Simple.

*Leaf base.*—Attenuate.

*Leaf apex.*—Acute.

*Leaf fragrance.*—None.

*Leaf venation.*—Pinnate, only midrib is conspicuous, 144A in color on upper surface, 147D in color on lower surface.

*Leaf margins.*—Finely serrate with an average of 18 teeth per cm of margin.

*Leaf arrangement.*—Alternate.

*Leaf attachment.*—Petiolate.

*Leaf surface.*—Glabrous and glossy on upper surface, glabrous and dull on lower surface.

*Leaf size.*—Average of 2.1 cm in length and 9 mm in width when mature.

*Leaf color.*—Newly expanded leaves upper surface; 144A, newly expanded leaves lower surface; 144B, mature leaves upper surface; between 137A and 147A but slightly darker, mature leaves lower surface; 147C.

*Stipules.*—Not present.

*Petioles.*—Average of 3.5 mm in length and 1 mm in diameter, 185B to 185C in color on young leaves and N170B to N170C in color on mature leaves, surface is glabrous and dull.

Inflorescence Description:

*Inflorescence type.*—Terminal panicle.

*Lastingness of inflorescence.*—Individual flowers last about 10 days.

*Inflorescence size.*—Average of 6.5 cm in length and 4.5 cm in width.

*Flower size.*—Average of 1.9 cm in height and 1.4 cm in depth.

*Flower fragrance.*—None detected.

*Flower number.*—Average of 15 per inflorescence, one inflorescence per stem.

*Flower aspect.*—Outward from peduncle.

*Flower bud.*—Oblong in shape, an average of 1.1 cm in length and 0.8 cm in width, color is a blend of 62C and 58C.

*Flower form.*—Tubular.

*Sepals.*—5, un-fused and recurved at apex, elliptic to obelliptic in shape, rounded apex, cuneate base, surface is glabrous, entire margins, color of upper and lower surface when opening and mature is a blend of 58B, 58C and 62C.

*Calyx.*—Rotate and spreading, an average of 1.2 cm in length and 8 mm in width.

*Sepals.*—5, spreading as the flower opens, an average of 1.2 cm in length and 4 mm in width, narrowly lanceolate in shape, entire margin, glabrous surface, rounded apex, cuneate base, color of upper and lower surface when opening and mature is a blend of 58B and 58C.

*Peduncle size.*—Round in shape, strong, extended from stem, an average of 6.5 cm in length (length of panicle) and 2 mm in diameter, glabrous surface, 58A to 58B in color.

*Petioles.*—Round in shape, held at about a 45° angle to peduncle, ranges from 0.4 to 2 cm in length and an average of 1.5 mm in diameter, glabrous surface, 58A to 58B in color.

Reproductive Organs:

*Gynoecium.*—1 pistil, about 1.5 cm in length, style and stigma are 145D in color.

*Androcoecium.*—5 stamens, filament is about 1.2 cm in length and 145D in color, pollen is moderate in abundant and 11C to 11D in color.

*Fruit/seeds.*—No fruit set (or seeds) were observed.

I claim:

1. A new and distinct cultivar of *Escallonia* plant named 'Jamie' as herein illustrated and described.

* * * * *